United States Patent [19]

McKinnie et al.

[11] 4,324,920
[45] Apr. 13, 1982

[54] PROCESS FOR THE PREPARATION OF ORTHO-(HYDROCARBYLTHIO)-PHENOLS

[75] Inventors: Bonnie G. McKinnie; Paul F. Ranken, both of Baton Rouge, La.

[73] Assignee: Ethyl Corporation, Richmond, Va.

[21] Appl. No.: 172,977

[22] Filed: Jul. 28, 1980

[51] Int. Cl.$^3$ ............................................. C07C 148/00
[52] U.S. Cl. ......................................... 568/54; 568/53
[58] Field of Search .......................................... 568/54

[56] References Cited

U.S. PATENT DOCUMENTS

| | | | |
|---|---|---|---|
| 2,745,878 | 5/1956 | Mairty | 568/54 |
| 2,831,898 | 4/1958 | Ecke et al. | 260/624 |
| 2,923,743 | 2/1960 | Delfs et al. | 568/54 |
| 2,923,745 | 2/1960 | Buls et al. | 260/624 |
| 3,200,157 | 10/1965 | Buls et al. | 260/624 |

OTHER PUBLICATIONS

B. Farah et al., J. Organic Chem., vol. 28 (1963), pp. 2807–2809, Alkyl-mercaptophenols by Sulfenylation of Phenols.
A. Pedersen et al., Tetrahedron, vol. 26, pp. 4449–4457 (1970) o-Hydroxyphenyl alkyl Sulfides, Sulfoxides and Sulfones.

*Primary Examiner*—Donald G. Daus
*Assistant Examiner*—D. G. Rivers
*Attorney, Agent, or Firm*—Donald L. Johnson; John F. Sieberth

[57] ABSTRACT

Disclosed is a process for the preparation of otho-(hydrocarbylthio)-phenols, having at least one hydrogen on a carbon atom ortho to a hydroxy group, with hydrocarbyl disulfides in the presence of catalytic amounts of aluminum phenoxide.

12 Claims, No Drawings

PROCESS FOR THE PREPARATION OF ORTHO-(HYDROCARBYLTHIO)-PHENOLS

INTRODUCTION

This invention relates to a process for the preparation of ortho-(hydrocarbylthio)-phenols. Such compounds are characterized by containing a hydrocarbylthio-group (RS—) ortho to a phenolic hydroxyl group.

BACKGROUND OF THE INVENTION

Ortho-(hydrocarbylthio)-phenols are useful compounds, e.g. as intermediates in the preparation of hypotensive drugs and agricultural chemicals such as plant protection agents, herbicides, pesticides and the like. U.S. Pat. No. 2,923,743 describes a process for the production of aryl-alkyl thioethers by reacting a dialkyl disulfide with aromatic compounds such as phenol, chlorophenol, p-cresol, 2-naphthol, etc., in the presence of suitable condensation agents, such as for example, aluminum chloride, aluminum bromide, ferric chloride, zinc chloride, tin tetrachloride, antimony pentachloride, boron fluoride and bleaching earth. At Column 1, lines 31-36, that patent discloses:

"These condensation agents can be added in different amounts. In general there should be added at least molecular amounts referred to the dialkyl disulfide but there can be used also higher amounts e.g. a 3-fold surplus of the condensation agent."

THE INVENTION

It has been found that ortho-substituted phenols can be prepared in good yields by contacting phenols, having at least one hydrogen on a carbon atom ortho to a hydroxy group, with hydrocarbyl disulfides in the presence of catalytic amounts of aluminum phenoxide, i.e. less than molecular or equivalent amounts of aluminum phenoxide. The process of this invention requires no solvent and makes use of cheap and available materials. Furthermore, the lower molecular weight, relatively volatile ortho-(hydrocarbylthio)-phenols producible by the process can be distilled directly from the reaction mixture thereby facilitating product separation, purification and recovery operations. Still further advantages will be apparent from the following disclosure.

In accordance with this invention there is provided a process for the preparation of ortho-substituted phenols which comprises contacting phenols having at least one hydrogen on a carbon atom ortho to a hydroxy group with a hydrocarbyl disulfide in the presence of an aluminum phenoxide catalyst, the molar ratio of the catalyst to the disulfide being less than 1, preferably between about 0.01 and 0.5 and most preferably between about 0.01 and 0.2. The process is normally conducted at a temperature within the range of from about 0° C. to about 500° C. at which the desired reaction takes place. Preferably the process is performed at a temperature of from about 100° C. to about 300° C. and most preferably from about 120° C. to about 200° C. With the process of this invention one mole of hydrocarbyl thiol (RSH) is formed as by-product for each hydrocarbylthio- group (RS—) substituted onto the phenol. Without being bound to a particular mechanism or theory, it appears that the reacting hydrocarbyl disulfide is split into two species or moieties, one being substituted onto the phenol the other forming the corresponding hydrocarbyl thiol by-product. In a particularly preferred embodiment the process of this invention is conducted in such a way that the hydrocarbyl thiol by-product is removed from the reaction vessel essentially as rapidly as it is formed. This can be accomplished for example by conducting the reaction at reflux temperatures and/or under reduced pressures (i.e. below atmospheric pressure) and/or under a sweep of an inert gas so that the hydrocarbyl thiol by-product evolved is rapidly removed or purged from the reaction vessel. In still another preferred embodiment the hydrocarbyl disulfide reactant is an aliphatic disulfide, most preferably a lower alkyl disulfide.

The aluminum phenoxide catalyst used in the practice of this invention can be formed in various ways. For example it can be formed by contacting aluminum metal, preferably in the form of turnings, powders, particles and the like, with the phenol at elevated temperatures (e.g. 100-200° C.) until cessation of hydrogen evolution. Another way of forming the catalyst used in this invention is by simply contacting an aluminum alkyl such as triethylaluminum with the phenol. Still another method of forming the catalyst used herein involves contacting aluminum chloride (i.e. $AlCl_3$) and the phenol at elevated temperatures, e.g. between 100° and 200° C. and purging the system of the hydrogen chloride generated during the preparation of the phenoxide catalyst. The source of the aluminum phenoxide catalyst does not materially affect the reaction and other methods known in the art for the formation of these compounds can be successfully employed herein. Exemplary methods for preparing aluminum phenoxide catalysts useful in the process of this invention appear in U.S. Pat. Nos. 2,831,898; 2,923,745 and 3,200,157. The preferred catalyst is aluminum tri-phenoxide, although the di-phenoxide catalyst, e.g., di-phenoxy aluminum chloride which may be formed in the reaction of aluminum chloride and phenol, can also be used in the practice of this invention.

Hydrocarbyl disulfides which may be employed in the practice of the present invention include aliphatic, cycloaliphatic and aromatic disulfides. Aliphatic disulfides include the saturated and unsaturated linear and branched aliphatic disulfides. They may be substituted in one or more positions with for example a halogen such as chlorine or bromine. Specific aliphatic disulfides which may be used herein are methyl disulfide, ethyl disulfide, methyl ethyl disulfide, n-butyl disulfide, sec-butyl disulfide, tert-butyl disulfide, propylene disulfide and 2-chloropentyl disulfide. The cycloaliphatic disulfides which may be used herein include the saturated and unsaturated disulfides which can be substituted with various substituents such as hydrocarbon substituents, halogen substituents and the like. Examples include cyclopentyl disulfide, cyclohexyl disulfide, the various 3-chlorocyclohexene disulfides and the like. Aromatic disulfides which can be used include substituted and unsubstituted aromatic disulfides. Specific examples include benzyl disulfide, p-tolyl disulfide, p-chlorophenyl disulfide and the like.

Phenols used herein can be mono- or poly-nuclear, e.g. the naphthols. The phenols can contain one or more hydroxy substituent as long as there is at least one hydrogen ortho to a hydroxy group on the phenol or hydroxy aromatic compound. The aryl portion of the hydroxy aromatic compound may be linked to or fused with other cyclic systems including heterocyclic systems such as those containing cyclo oxygen, nitrogen and sulfur rings. For example, the hydroxy aromatic can be any of the isometric hydroxy-substituted derivatives of benzene, naphthalene, anthracene, phenanthrene, indene, isoindene, benzofuran, isobenzofuran, thionaphthene, indole, isoindole, indolenine, 2-isobenzazole, 1,2-benzodiazole, 1,3-benzodiazole, indiazene, 1,3-benzoisodiazole, 1,2,3-benzotriazole, benzisoxazole, benzoxadiazole, 1,2-benzopyran, 1,4-benzopyran, 1,2-benzopyrone, quinoline, isoquinoline, 1,3-benzodiazine, 1,2-benzisoxazine, acenaphthene, fluorene, dibenzopyrrole, xanthene, thianthrene, phenothiazine, phenoxazine, naphthacene, chrysene, pyrene, triphenylene, biphenyl, phenylpyridine, and the like, wherein the hydroxyl group is bonded to a nuclear carbon atom of a benzene ring.

The process is also applicable to aryl hydroxy compounds having more than one hydroxyl radical bonded to a nuclear aromatic carbon atom. For example, the process can be applied to such polyhydroxy aromatics as hydroquinones, resorcinols, catechols, 1,3-dihydroxy naphthalenes, phloroglucinols, 2,2'-dihydroxydiphenyl, 2,4,4'-dihydroxydiphenyl, and the like.

Substituents other than hydroxyl groups can be present in the hydroxy aromatic compounds as lone as they do not interfere with the course of the reaction. That is to say, the other substituents should be relatively inert under the conditions of the reaction. For example, any of the previously mentioned aromatics may be substituted in a variety of positions with alkyl radicals, aralkyl radicals, cycloalkyl radicals, chlorine, bromine, iodine, fluorine, and the like. A few representative examples of these using the simpler aromatic structure are p-chlorophenol, p-nitrophenol, 4-bromo-1-naphthol, p-(4-chlorophenyl)phenol, β-chloro-7-hydroxy-coumarone, 2-acetoxy-7-hydroxy-indolenine, 3-n-dodecyl-7-hydroxy-benzisoxazole, 8-hydroxy-5-methyl-1,2-benzopyran, 5-sec-octadecyl-8-hydroxy-isocoumarin, and the like.

The rection proceeds very well when the hydroxy aromatic compound is a hydroxy-substituted mononuclear aromatic. As previously, these phenol type materials can be substituted with other groups as long as they do not interfere with the course of the reaction. A preferred class of such mononuclear hydroxy aromatics are those which can be represented by the formula:

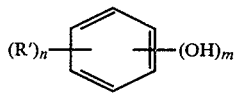

where n is an integer from 0-2, m is an integer of from 1-2 and wherein R is selected from the group consisting of alkyl radicals containing from 1-50 carbon atoms, aralkyl radicals containing from 7-20 carbon atoms and cycloalkyl radicals containing from 5-20 carbon atoms, with the proviso that at least one ortho position relative to a hydroxyl group is unsubstituted and available for substitution by a hydrocarbylthio group. Some examples of these are: phenol, catechol, resorcinol, phlorogluncinol, hydroquinone, 3,5-methylphenol, 2,6-dimethoxyhydroquinone, 3-methyl catechol, p-cresol, m-cresol, p-pentacontyl phenol, 2,4-didodecyl phenol, o-cyclohexyl phenol, 3-cyclooctyl phenol, p-(4-sec-dodecylcyclohexyl)phenol, 2,5-dimethyl phenol, m-sec-eicosyl phenol, p-(4-tridecylbenzyl) phenol, 4-(3,5-di-sec-heptylcyclohexyl)phenol, and 2-sec-pentacontyl hydroquinone.

Mononuclear phenols can be used in which one position ortho to the phenoxide oxygen atom is substituted with a radical selected from the group consisting of primary and secondary alkyl radicals containing from 1-50 carbon atoms, cycloalkyl radicals containing from 6-20 carbon atoms and primary and secondary aralkyl radicals containing from 7-20 carbon atoms. These are phenols having the formula:

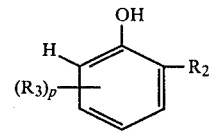

wherein p is an integer from 0-1, $R_2$ is selected from the group consisting of primary and secondary aliphatic alkyl radicals containing from 1-50 carbon atoms, primary and secondary aralkyl radicals containing from 7-20 carbon atoms, mononuclear aryl radicals containing from 6-20 carbon atoms and cycloalkyl radicals containing from 6-20 atoms. Some examples of the phenolic starting materials are:
o-sec-butylphenol,
2,5-diethylphenol,
o-ethylphenol,
2,4-di-sec-butylphenol,
2,4-dimethylphenol,
2-(α-methylbenzyl)phenol,
2-cyclohexyl-p-cresol,
2-(3,5-di-tert-butyl-cyclohexyl)phenol
2-sec-pentacontylphenol,
2-(α-methyl-4-dodecylbenzyl)phenol,
2-phenylphenol,
2-(4-tetradecylphenyl)phenol
2-(3,5-di-sec-heptylphenyl)phenol,
2-triacontylphenol,
2-isopropylphenol,
2,4-di-sec-dodecylphenol, and
2-(α-methyl-4-sec-amylbenzyl)phenol.

Phenols which may be used in the process of this invention further include the triophenols. Examples include thiophenol (benzene, 1-mercapto-), benzene, 1-mercapto-4-methyl, benzene, 1-mercapto-4-chloro-2-ethyl and the like.

A particularly preferred embodiment of this invention involves reaction (i) a mononuclear, monohydric phenol having in the molecule up to about 12 carbon atoms and up to two chlorine atoms and having at least one of its ortho positions unsubstituted and available for alkylthiolation, with (ii) a lower alkyl disulfide, i.e. each alkyl group has from 1 to about 6 carbon atoms, using an aluminum phenoxide catalyst in the manner described above. Thus in this embodiment use is made of such phenols as phenol, the cresols, the xylenols (except the 2,6 isomer), the mono- and di-chlorophenols (except the 2,6 isomer), the mono- and diethylphenols (except the 2,6 isomer), the mono- and di-propyl (or isopropyl) phenols (except the 2,6 isomer), the butyl, amyl, and hexyl phenols, 2,3,4-, 2,3,5- and 2,4,5-trimethylphenols, 2,3,4,5-tetramethylphenol, and any of the foregoing alkylphenols in which there are one or two chlorine atoms substituted on the ring (again provided there is a free ortho position for alkylthiolation). It is especially desirable to perform this process under conditions whereby the alkyl mercaptan by-product is removed from the reaction mixture during the course of the reaction.

In practicing the process of this invention the hydrocarbyl disulfide is normally added to the phenol-aluminum phenoxide mixture although the order of addition is not critical. Once the phenol and hydrocarbyl disulfide have been contacted in the presence of the catalyst the reaction is allowed to proceed at temperatures and times which can vary depending upon such considerations as the boiling point of the hydrocarbylthiol generated during reaction, the percent yield of product desired, the melting point of the reactants and the like. In general, when the reaction is carried out at atmospheric pressure, temperatures slightly above the boiling point of the hydrocarbyl disulfide are employed. In a particularly preferred aspect, the mixture is maintained at or near its reflux temperature. Of course if pressures below atmospheric pressure are employed the corresponding temperature may also be decreased. In a preferred embodiment as much of the hydrocarbylthiol by-product as is feasible is removed, e.g. by vacuum distillation and the like. Reaction times of up to 20 hours and more can be employed herein.

Although some para-substituted as well as di-substituted products are formed in the reaction, they are normally high boiling and as a consequence are easily separable from the lower boiling ortho-substituted product, e.g. by distillation of the product.

As noted above, the process of this invention is useful in the formation of chemical intermediates having wide utility. For example, British Pat. No. 1,544,872 describes the use of orthothiomethylphenol to form hypotensive drugs.

In practicing this invention a broad range of proportions of reactants can be utilized. That is, the relative amounts of phenol to the disulfide can vary widely; however, the relative proportion normally falls within the range of from about 5:1 to about 1:5. Furthermore, while the process of this invention can be carried out without the use of solvents or diluents they may nevertheless be used, if desired, so long as they are inert to the reaction disclosed herein. The process is preferably carried out under substantially anhydrous conditions, but conditions wherein trace or small amounts of water are present can be used. Accordingly, an inert atmosphere is normally employed in the present process.

The invention will be still further apparent from the following illustrative examples.

EXAMPLE 1

Preparation of Ortho-(Methylthio)-Phenol

To phenol (20 grams, 0.28 moles) was added powdered aluminum (0.76 grams, 0.03 moles). This mixture was heated to 140° C. and then cooled rapidly to 110° C. The mixture was then heated to 150° C. and the resulting slurry was cooled followed by the addition of methyldisulfide (20 ml, 0.22 moles). This mixture was then refluxed under nitrogen for 5 hours at 120° C. to 128° C. Vapor Phase Chromatography (VPC) showed the resulting mixture to contain phenol, ortho-(methylthio)-phenol, and para-(methylthio)-phenol in a molar ratio of 76:15:9, respectively.

EXAMPLE 2

Preparation of Ortho-(Methylthio)-Phenol

To phenol (30 grams, 0.3 moles) heated to 140° C. was added 5 mesh aluminum (0.64 grams, 0.02 moles) in three equal portions. The reaction proceeded smoothly to yield a grayish-black solution to which methyldisulfide (20 ml, 0.22 moles) was added and this mixture was refluxed in an oil bath at 150° C. overnight. VPC analysis showed that the relative mole percent of phenol: ortho-(methylthio)-phenol: para-(methylthio)-phenol was 51.8:32.7:15.5.

EXAMPLE 3

Preparation of Ortho-(Methylthio)-Phenol

To freshly distilled phenol (124.4 grams, 1.31 moles) heated to 140° C. was added 5 mesh aluminum (2.5 grams, 0.1 moles) in small portions. When hydrogen evolution ceased, the mixture was cooled to 120° C. and methyldisulfide (80 ml, 0.9 moles) was then added. The mixture was heated in a 140° C. oil bath and refluxed overnight at about 126° C. This mixture was then further heated for 3 hours at 165° C. and then distilled to yield 113.6 grams of product having a boiling point of 78° C. at 10 mm of mercury to 85° C. at 4 mm of mercury pressure. VPC analysis showed that the product contained 46.6 weight percent ortho-(methylthio)-phenol (a 43 percent yield), 50.7 weight percent phenol and 0.4 percent para-(methylthio)-phenol. Fractionation through a 0.7×30 cm column packed with glass helices gave 98.5 percent pure ortho-substituted product which boiled at 128° C. under 60 mm of mercury. This column was used in all fractionations unless otherwise indicated.

EXAMPLE 4

Preparation of Ortho-(Methylthio)-Phenol

To dried phenol (210 grams, 2.33 moles) heated to 140° C. was added aluminum (4.2 grams, 0.16 moles) in small portions. After cessation of hydrogen evolution the mixture was heated to 160° C. and methyldisulfide (132 ml, 1.48 moles) was added drop-wise at 150° C. to 160° C. over a period of 4 hours. This mixture was heated at 155° C. with stirring overnight and was then further heated at 165° C. for an additional 2 hours. The product was adiabatically flashed to give 202 grams of a liquid which was shown by VPC to contain 43.0 weight percent of ortho-(methylthio)-phenol, 0.51 weight percent para-(methylthio)-phenol and 49.8 weight percent phenol. Distillation of the liquid product yielded 80.2 grams of a liquid which was shown by VPC to contain 95 weight percent of ortho-(methylthio)-phenol and 5 weight percent phenol.

EXAMPLE 5

Preparation of Ortho-(Methylthio)-Phenol

A mixture of phenol (402 grams, 4.2 moles) and toluene (60 ml) was distilled to remove all toluene thereby yielding substantially anhydrous phenol. To the phenol, aluminum turnings (7.5 grams, 0.28 moles) were slowly added at 125° to 140° C. After cessation of hydrogen evolution, methyldisulfide (250 ml, 2.8 moles) was added and the resulting mixture was refluxed overnight at about 170° C. The mixture was then further heated at 170° to 185° C. for 3 hours. All volatile materials were then removed by vacuum evacuation at 20 mm Hg at 170° C. The unreacted phenol was removed by distillation through a 16"×½" heated column packed with glass helices. The residue, containing predominately the product ortho-(methylthio)-phenol, was distilled through a 7 cm Vigreax Column yielding 158 grams of the product (b.p. 115°–117° C. at 35 mm psig; 40.0 percent yield).

EXAMPLE 6

Preparation of Ortho-(Ethylthio)-Phenol

To freshly distilled phenol (50.6 grams, 0.54 moles) was added aluminum turnings (1.03 grams, 0.04 moles) and the mixture was heated at 140° to 150° C. until cessation of hydrogen evolution. To this mixture was added ethyldisulfide (44 ml) and the mixture was heated at 170° C. in an oil bath overnight. The mixture was then further heated at 190° C. for 3 additional hours and then vacuum flashed at 5 mm Hg at 180° C. to yield a yellow oil. VPC showed 5 area percent ethyldisulfide, 52 area percent phenol, 36 area percent ortho-(ethylthio)-phenol, 4 area percent para-(ethylthio)-phenol and 1.2 percent di-(ethylthio)-phenols. This oil was distilled through a packed column as in Example 3 and the third cut had a boiling point of 87° to 89° C. at 6 to 8 mm Hg. This cut had a total weight of 13.21 grams and was shown by NMR to be ortho-(ethylthio)-phenol for a 24 percent isolated yield.

EXAMPLE 7

Preparation of 2-Ethylthio-5-Ethylphenol

To freshly distilled 3-ethylphenol (100 grams, 0.82 moles), was added aluminum turnings (1.62 grams, 0.06 moles) and the mixture was heated at 175° to 195° C. until hydrogen evolution had ceased. Ethyldisulfide (63 grams, 0.515 moles) was then added in one portion at 150° C. This mixture was then heated at 175° to 180° C. for 18 hours and then for about 7 hours at 196° C. The resulting mixture was hydrolyzed with 3 N HCl, extracted with diethylether, washed with water and dried over magnesium sulfate. Distillation of the mixture followed by a redistillation through a packed column gave, after removal of by-products and starting materials, 8.15 grams of 2-ethylthio-5-ethylphenol as verified by $^1$H and $^{13}$C NMR.

EXAMPLE 8

Preparation of 4-Chloro-2-(Methylthio)-Phenol

A mixture of para-chlorophenol (100 grams, 0.78 moles) and cyclohexane (50 ml) was distilled free of cyclohexane to remove any residual water in the para-chlorophenol. The para-chlorophenol was heated at 160° to 180° C. and aluminum turnings (1.5 grams, 0.06 moles) were slowly added. After cessation of hydrogen evolution, methyldisulfide (46 ml) was added to the mixture and heated at reflux (ca. 152° C.) overnight. The temperature was then increased to 180° C. for 2 additional hours. The mixture was hydrolyzed by the addition of b 1N HCl, extracted with diethyl ether and dried over sodium sulfate. Concentration and distillation through a packed column gave, after removal of the para-chlorophenol, 52.25 grams of 4-chloro-2-(methylthio)-phenol product. The result was confirmed by NMR analysis, the overall yield being 55 percent.

EXAMPLE 9

Preparation of Ortho-(Methylthio)-Phenol

In this instance the aluminum phenoxide catalyst was formed by the drop-wise addition of triethylaluminum (2.0 ml, 0.01 moles) to phenol (20 grams, 0.2 moles) at ambient temperature. Subsequently methyldisulfide (20 ml, 0.2 moles) was added and the resulting mixture heated at reflux for 5.75 hours. The progress of the reaction and the results obtained as determined by VPC analysis are shown in the table below.

TABLE

| Time (Hrs.) | Temperature of Reflux | Molar Ratio of Phenol: Ortho-(Methylthio)-Phenol: Para-(methylthio)-Phenol |
|---|---|---|
| 0 | 123° | —* |
| 1 | 123° | 90/6.5/3.5 |
| 2 | —* | 82/11.6/6.3 |
| 3¼ | —* | 68/21/11.1 |
| 4¼ | 140° | 51/31/17.5 |
| 5¾ | 165° | 34/45.5/20.5 |

*No measurement was taken.

EXAMPLE 10

Preparation of Ortho-(Methylthio)-Phenol

In this instance the aluminum phenoxide catalyst was formed by the addition of aluminum chloride (AlCl$_3$, 1.4 grams, 0.01 moles) to phenol (20 grams, 0.2 moles). The mixture was then heated to 150° C. for about 15 minutes. The mixture was then cooled to about 100° C. and methyldisulfide was added (20 ml, 0.2 moles). After heating the mixture at reflux (128° C.) for one hour and forty-five minutes the reaction temperature was raised to 138° C. and the mixture heated overnight (about 18 hours). The resulting product was analyzed by VPC and the molar ratio of phenol:ortho-(methylthio)-phenol:para-(methylthio)-phenol was found to be 41:39:20.

EXAMPLE 11

Preparation of 4-Methyl-2-(Methylthio)-Phenol

A mixture of para-cresol (65 grams, 0.60 moles) and toluene (20 ml) was distilled until the mixture was free of toluene. Aluminum turnings (1.1 grams, 0.04 gram atoms) were then added to the dried para-cresol and this mixture was heated at 150°–160° C. until cessation of hydrogen evolution. Methyldisulfide (36 ml, 0.4 moles) was added and the mixture heated at reflux (about 160° C.) overnight. The mixture was refluxed for another additional 4 hours and was then flashed under a vacuum. The flashed mixture was then distilled through a 0.7×30 cm packed column to yield 30.3 grams of 4-methyl-2-(methylthio)-phenol, a 55 percent yield. Subsequently, MMR analysis verified the identity of the compound.

What is claimed is:

1. A process for the preparation of ortho-substituted phenols which comprises reacting a phenol having at least one hydrogen on a carbon atom ortho to a hydroxy group with a hydrocarbyl disulfide in the presence of an aluminum phenoxide catalyst so that an ortho-(hydrocarbylthio)-phenol is prepared, the molar ratio of said catalyst relative to said disulfide being between about 0.01 and 0.5.

2. A process of claim 1 wherein said process is carried out at a temperature of from between about 100° and about 300° C.

3. A process of claim 1 wherein said molar ratio is between about 0.01 and 0.2.

4. A process of claim 1 wherein the hydrocarbyl thiol formed as by-product in the reaction is removed from the reaction vessel essentially as rapidly as it is formed.

5. A process of claim 1 wherein said hydrocarbyl disulfide is an aliphatic thiol.

6. A process of claim 5 wherein said disulfide is an alkyl disulfide.

7. A process of claim 6 wherein said alkyl disulfide is methyl disulfide.

8. A process of claim 1 wherein said aluminum phenoxide is formed in situ by contacting aluminum with said phenol.

9. A process for the alkylthiolation of a phenol which comprises reacting (i) a mononuclear, monohydric phenol having in the molecule up to about 12 carbon atoms and up to 2 chlorine atoms substituted on the ring and having at least one of its ortho positions unsubstituted and available for alkylthiolation with (ii) a lower alkyl disulfide in the presence of an aluminum phenoxide catalyst so that said phenol is alkylthiolated, the molar ratio of said catalyst relative to said disulfide being between about 0.01 and 0.5.

10. A process of claim 9 wherein the lower alkyl mercaptan by-product of the reaction is removed from the reaction mixture during the course of the reaction.

11. A process of claim 10 wherein the reaction is performed at a temperature within the range of from about 120° to about 200° C.

12. A process of claim 9 wherein said monohydric phenol is phenol or cresol.

* * * * *